US006786244B1

(12) United States Patent
Jones

(10) Patent No.: US 6,786,244 B1
(45) Date of Patent: Sep. 7, 2004

(54) APPARATUS AND METHOD TO ENHANCE RESERVOIR UTILIZATION IN A MEDICAL INFUSION DEVICE

(75) Inventor: Steven Paul Jones, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 10/403,156

(22) Filed: Mar. 31, 2003

(51) Int. Cl.[7] .................................................. B65B 1/04

(52) U.S. Cl. .............................. 141/2; 141/18; 141/21; 604/183

(58) Field of Search ............................. 141/2, 18, 21, 141/98, 28, 99, 100, 102, 104, 285; 604/183, 133, 246, 184, 185, 186, 190

(56) References Cited

U.S. PATENT DOCUMENTS

| 3,650,093 | A | * | 3/1972 | Rosenberg .................. 604/123 |
| 4,904,243 | A | * | 2/1990 | Bruera ....................... 604/183 |
| 5,545,152 | A | | 8/1996 | Funderburk et al. ........ 604/283 |
| 6,065,727 | A | * | 5/2000 | Fitzgerald et al. .......... 248/302 |
| 6,360,784 | B1 | * | 3/2002 | Philippens et al. ............ 141/2 |
| 6,685,674 | B2 | * | 2/2004 | Douglas et al. ........ 604/167.05 |

* cited by examiner

Primary Examiner—David A. Scherbel
Assistant Examiner—Khoa D. Huynh
(74) Attorney, Agent, or Firm—Robert R. Williams

(57) ABSTRACT

A method and apparatus are disclosed that allow more efficient volume use of a reservoir used in medical infusion devices, such as insulin pumps. The invention provides for having a full reservoir and a full tubing composite when infusion of medication into a patient begins, allowing a volume of medicine substantially equal to the volume of medication in the full reservoir to be infused into the patient.

7 Claims, 14 Drawing Sheets

APPARATUS AND METHOD TO ENHANCE RESERVOIR UTILIZATION IN A MEDICAL INFUSION DEVICE

RELATED PATENTS

U.S. Pat. No. 5,545,152, by Jeffery V. Funderburk and Deborah C. McIntyre (hereinafter Funderburk) discloses a "quick-connect coupling for a medication infusion system". Several references to this patent are made in the present invention.

FIELD OF THE INVENTION

The present invention relates to devices used to infuse liquid medication into a patient. More specifically, this invention relates to miniaturization of such devices.

DESCRIPTION OF RELATED ART

Insulin dependent diabetes mellitus (IDDM) is caused by the autoimmune destruction of the insulin producing islets of Langerhans in the pancreas. Insulin replacement therapy is the interim treatment for IDDM until such time as islet transplants, stem cell treatments, or other improved treatments become feasible. Insulin lowers the concentration of glucose in the blood, while food—in particular, carbohydrates—raises the concentration of glucose in the blood. The challenge of insulin therapy is to administer food and insulin in a manner that maintains blood glucose concentrations in an acceptable range, avoiding hypoglycemia and hyperglycemia.

Hyperglycemia (high blood glucose concentration) has adverse long-term consequences for the body. These consequences include kidney damage leading to kidney failure, microaneurisms in the retina causing blindness, and the blocking of capillaries in the extremities causing an inability to heal wounds and subsequent gangrene. Hypoglycemia (low blood glucose concentration) has an immediate adverse consequence of reduced brain function that leads to confusion and an inability to reason, remember, or react. In the extreme, hypoglycemia causes seizure, coma, and death.

The first insulin used by diabetes patients was regular insulin taken from beef or pig pancreases. This insulin lasts for about six hours, so that patients were required to inject it three or four times per day. After World War II, longer acting insulin was developed by binding regular insulin to protamine and zinc. Regular insulin dissociates slowly from protamine and zinc, extending insulin action to twelve hours for intermediate acting insulin and twenty-four hours for very long acting insulin. Patients enjoyed reducing injections to one per day, but were required to modify their eating to a snack-all-day regimen to avoid hypoglycemia. The one daily insulin dose was adjusted as needed to reduce the incidence of both hypoglycemia and hyperglycemia.

The development of portable blood glucose meters encouraged the development of more sophisticated insulin therapy regimens. One of these regimens is the split/mixed regiment that consists of two daily doses of mixed regular and intermediate acting insulins taken before breakfast and dinner. These four insulin therapy components are adjusted using blood glucose values measured before each meal and at bedtime. Patients using the split/mixed regimen are required to eat substantially the same meals every day so that the four insulin components may be adapted to the consistent meal pattern over time. Patients on the split/mixed regimen are not only faced with a consistent pattern of what they eat in terms of amount of food, but are also required to eat their meals at particular times. Delay of a meal will result in the patient suffering hypoglycemia A more recent development in insulin regimen is the basal/bolus regimen, which provides far more flexibility in quantity and timing of meals. The basal/bolus program attempts to emulate the method by which an intact pancreas controls blood glucose. Normally, the intact pancreas produces a steady supply of basal insulin to accommodate the body's basic insulin needs for glucose secreted at a relatively constant rate from the liver. The pancreas handles meals by releasing a sharp impulse of bolus insulin to accommodate a rapidly rising blood glucose resulting from transformation of carbohydrates (and, to a lesser extent, other food items, especially protein) into blood glucose.

In the basal/bolus regimen, the basal insulin releases are emulated by a once a day injection of a long acting insulin, such as Lantus®, a product of Aventis Pharmaceuticals, or Ultralente®, a product of Eli Lilly and Company. Ultralente is sometimes injected twice daily. These long acting insulins provide the body with a relatively constant supply of insulin. The bolus insulin releases are emulated by bolus injections of fast acting Humalog® (lispro), or other fast acting insulin. The amount of fast acting insulin taken in an injection must be proportional to the amount of carbohydrate taken with the meal. Some diabetics are able to further fine-tune the injection by calculating the amount of protein, which has a smaller effect on the rise of blood glucose concentration.

To illustrate the basal/bolus regimen in an example, assume a typical diabetic who requires 0.5 units per hour of basal insulin. This person will need a 12-unit injection of long acting insulin daily to cover his or her basal requirements. Timing of such an injection is not critical, and in fact, the long acting insulin is often mixed with the fast acting insulin in one of the bolus injections. Further assume that this typical diabetic's blood glucose is raised 4 mg/dl (blood glucose concentrations are measured in milligrams per deciliter) for every gram of carbohydrate eaten. This is known as carbohydrate sensitivity. Assume also that a unit of insulin (insulin is measured in "units") reduces this typical diabetic's blood glucose concentration by 40 mg/dl. This is known as insulin sensitivity. The diabetic sits down at a meal and adds up the total grams of carbohydrates in the meal. Assume the meal consists of 80 g of carbohydrates. The diabetic would compute the increase in blood glucose concentration to be (4 mg/dl/g)*(80 g)=320 mg/dl. The diabetic would then compute the amount of bolus insulin required to accommodate, or "cover" this increase, knowing his or her insulin sensitivity. (320 mg/dl)/(40 mg/dl/unit)=8 units. The diabetic would therefore inject 8 units of fast acting insulin before eating the meal.

In practice, exercise, stress, and even unknown factors cause the above calculations to be only approximations. The diabetic, in his or her basal/bolus regimen, usually also needs to adjust the bolus dose taken based upon a blood glucose reading taken prior to the meal. A typical desired target for a diabetic's blood glucose concentration prior to a meal is 100 mg/dl. "Normal" blood glucose concentration range is 80 mg/dl to 120 mg/dl. A blood glucose concentration of 70 mg/dl or lower is usually considered to be hypoglycemic. A blood glucose concentration of 40 mg/dl is dangerously hypoglycemic and the diabetic is usually seriously impaired when his or her blood glucose concentration is at that level. A sustained blood glucose concentration of 20 mg/dl or lower is considered to expose the diabetic to permanent brain damage.

Suppose that, in the example above, the diabetic's pre-meal blood glucose concentration were 180 mg/dl. The diabetic would recognize that as being 80 mg/dl above the desired concentration of 100 mg/dl. Using the insulin sensitivity in the example, the diabetic would compute the additional insulin required as (80 mg/dl)/(40 mg/dl/unit)=2 units. In the example, the diabetic would then take a 10-unit bolus; 8 for the carbohydrates in the meal, and 2 more to "cover" the fact that the premeal blood glucose concentration was 80 mg/dl above target. If, in the example, the premeal blood glucose concentration were 80 mg/dl (versus a 100 mg/dl "target"), the diabetic would compute a 0.5 unit negative adjustment (80 mg/dl-100 mg/dl)/(40 mg/dl/unit), and thus take a bolus of 7.5 units with the meal instead of 8 units.

Insulin pumps are mechanisms that allow the basal/bolus regimen to be practiced even more effectively. An insulin pump contains a reservoir of fast acting insulin. Insulin is pumped through a tube from the reservoir into the diabetic. A computer within the pump, with which the diabetic interacts, controls the insulin pump. The diabetic programs in a "basal profile" which tells the pump how much of the fast acting insulin per unit time period to infuse into the diabetic. The pump then infuses this amount into the diabetic in a series of small infusions. In the example above, an infusion rate of 0.5 units per hour was assumed. In practice, this number varies considerably from one individual to the next In some individuals, the rate also needs to vary during the course of a day. In particular, many diabetics find they need a higher rate of infusion for several hours before breakfast. The series of small infusions of fast acting insulin replaces the single injection of long acting insulin as described above. Some insulin pumps infuse a constant microdose at varying time intervals. For example, if the infusion rate is 0.5 units/hour, some insulin pumps will infuse a 0.1 unit microdose five times in a one-hour period. Other pumps will infuse a microdose of varying size, but at constant time intervals. For example, such pumps might infuse a microdose every 3 minutes. The size of each microdose, following the 0.5 unit/hour example, would be (0.5 units/hour)/(20 microdoses/hour), or 0.025 units/microdose.

At a meal, the diabetic makes the same calculations described above for bolus determination, and interacts with the pump to cause it to infuse the proper bolus of fast acting insulin to cover the carbohydrates of the meal, plus or minus any correction that may be needed.

An early insulin pump prototype was introduced in 1963, and was the size of a large backpack. Of course, such a device was impractical because of its size and weight. However, it did demonstrate feasibility of insulin pumps from the standpoint of keeping patients' blood glucose concentrations in a desirable range.

In the 1970's miniaturization had progressed to where an insulin pump that was roughly the size of a brick, and weighing about a pound was marketed. The size and weight of such a device was still a very major inhibitor to widespread use. Diabetics simply refused to wear such a heavy and cumbersome device.

In 1980, further miniaturization had reduced the size of a commercial insulin pump to 3.4"×6.3"×1", weighing 9.6 ounces. Although about ⅓ the size of its predecessors, this pump, too, was too large and awkward for most diabetics.

In the early 1990's, MiniMed Corporation (now owned by Medtronics Corporation) introduced an insulin pump roughly the size of a pager. The pump was 2"×3.4"×0.8" and weighted only 3.6 ounces. This pump, and successors having additional features, but of approximately the same physical size, became very popular. Being of "pager size", these pumps could be worn on belts without being excessively awkward or conspicuous.

Hiding an insulin pump, however, has proved desirable to many people. In response to this desire, a market has arisen for products that hold an insulin pump under clothing. A product made of elastic material and having a pump-sized pouch can be purchased to hold a pump on a user's calf or thigh. Another product hides a pump in a woman's bra.

Pump manufacturers have recognized that "small is better". However, roughly half the volume of modem pumps is reserved for a reservoir that holds the insulin. Typically, such reservoirs hold 3cc of insulin, which contains 300 units at the insulin concentration most widespread today (U-100). Although more concentrated insulin is known today, and in fact is used in experimental insulin pumps surgically implanted in a diabetic's body, concern exists with such insulins regarding insulin crystallization in the relatively long tubing through which the insulin must flow between the pump and the body. Such more concentrated insulins are not currently being used in external insulin pumps.

Responsive to demand for smaller insulin pumps, some recent designs have reduced the volume of the insulin reservoir. The MiniMed Paradigm® insulin pump reservoir, for example, only holds 176 units of insulin, instead of the 300 unit reservoirs that are commonly used in larger pumps. The MiniMed Paradigm® has succeeded in attaining a 37% reduction in pump size, largely due to the use of the smaller reservoir.

Use of a smaller reservoir, however, can result in required more frequent changes of the reservoir and tubing. Most diabetics change their reservoir, tubing, and infusion set (collectively called "disposables") approximately every three days. An infusion set comprises a canula inserted into the body. The infusion set also comprises tape or other means to attach the infusion set to the body. Less frequent changes raises risk for infection and scarring of tissue where the infusion set is inserted into the body. More frequent change increases the annual cost of treatment.

The conventional process of changing a reservoir, tubing, and infusion set comprises the steps of filling the reservoir from a vial, attaching the tubing to the reservoir, and filling the tubing from the reservoir. A 42" length of tubing holds approximately 26 units of insulin. In addition, the infusion set requires approximately 1 to 3 units of insulin. The previously used tubing and infusion set and the insulin they contain, are discarded when changing the disposables. After filling a 42" tubing and the infusion set from the reservoir, the reservoir contains 26 fewer units of insulin than were drawn from the vial, further, less the 1 to 3 units that were discarded in the infusion set. In the case of the MiniMed Paradigm®, although 176 units were drawn from the vial to fill the 176-unit reservoir, less than 150 units can be infused into the diabetic. The remaining units are discarded, along with the tubing and infusion set, when the disposables are replaced. Almost ⅓ of type-1 diabetics require more than 50 units/day of U-100 insulin. Furthermore, insulin pumps are beginning to be marketed to type-2 diabetics. Type-2 diabetics are often "insulin resistant", that is, needing more insulin per gram of carbohydrate, and therefore require more insulin per day than type-1 diabetics. Any diabetic requiring even slightly more than 50 units/day, in the case of the Paradigm® pump, will need to change their disposables more often than every three days, incurring unnecessary expense, as well as the inconvenience of changing the disposables more frequently.

Although insulin infusion pumps were used for exemplary purposes above, any medical infusion device, especially medical infusion devices that must be worn by patients, are desirably as small as possible, and therefore, share the same problem of making the best use of the volume of the reservoir that holds the medication.

Therefore, a need exists to make more efficient use of the capacity of a reservoir in a medical infusion device.

SUMMARY OF THE INVENTION

The present invention discloses an apparatus and method that allows a quantity (volume) of medication substantially equal to the entire volume of a reservoir to be infused into the patient.

In a first embodiment, a method is disclosed to allow infusion of a quantity of medication that is substantially equal to the entire quantity of medication held in a reservoir, wherein medication from a vial of medication is drawn through a quick-release syringe into a tubing coupled to a reservoir, to fill the volume of the tubing, and, optionally, some of the volume of the reservoir. Subsequently, the tubing is detached from the reservoir, a reservoir syringe is attached to the reservoir, and the reservoir is "topped off" with medication from the vial. Then the reservoir syringe is detached from the reservoir. Finally, the tubing is reattached to the reservoir, an infusion set is coupled to a distal end of the tubing, and the infusion set is primed (filled) with medication. At that point, a cannula on the infusion set is inserted into the patient's body, and the infusion set is affixed by adhesive or other means to the patient's body. Because both the reservoir and the tubing are full, a volume of medication equal to substantially all of the volume of the reservoir can be infused into the patient.

In another embodiment, a method that will allow infusion of a quantity (volume) of medication that is substantially equal to the entire volume of a reservoir, is disclosed wherein medication from a vial of medication is drawn through a reservoir syringe attached to a reservoir. Subsequently, the reservoir syringe is detached, and a tubing is attached to the reservoir. The tubing is filled from the reservoir. Then, the tubing is detached from the reservoir, the reservoir syringe is reattached to the reservoir, and the reservoir is "topped off" from the vial of medication. The reservoir syringe is again detached. The tubing is reattached to the reservoir. An infusion set is coupled to a distal end of the tubing, and the infusion set is primed with medication. At that point, a cannula on the infusion set is inserted into the patient's body, and the infusion set is affixed by adhesive or other means to the patient's body. Because both the reservoir and the main tubing are full, a volume of medication equal to substantially all of the volume of the reservoir can be infused into the patient.

The Funderburk patent cited earlier discloses a "quick-connect coupling for a medication infusion system". A quick-release syringe improvement of the coupling disclosed in Funderburk is disclosed herein as an apparatus used in the present invention. The novel quick-release syringe disclosed couples with a quick-release portion on a distal end of the tubing. Medication is drawn from a vial of medication through the quick-release syringe, filling the tubing and, optionally, a portion of a reservoir.

In another apparatus embodiment, a tubing has a first quick-release coupling portion at a proximal end of the tubing and a second quick-release coupling portion at a distal end of the tubing. A short air elimination tubing is disclosed that has a first end suitable for attaching to a reservoir and a second end having a third quick-release coupling portion suitable for coupling to the first quick-release coupling portion. The short air elimination tubing allows removal of any air that might enter when the first end of the air elimination tubing is attached to the reservoir. Advantageously, the air elimination tubing is short and contains only a small amount of medication, preferably less than approximately 1% of the volume of a reservoir in a medication infusion device. Although the volume of the air elimination tubing is preferably approximately 1% or less of the volume of the reservoir, longer air eliminating tubings can be used, although with reduced advantage of the invention.

Even if the air elimination tubing volume is approximately 3% or 6% of the volume of the reservoir, a larger quantity of medication can be infused into the patient from a given reservoir than when using prior methods.

DETAILED DESCRIPTION OF THE PREFERRED EMBODIMENTS

Having reference now to the figures, the invention will now be described in detail.

Figure 1:
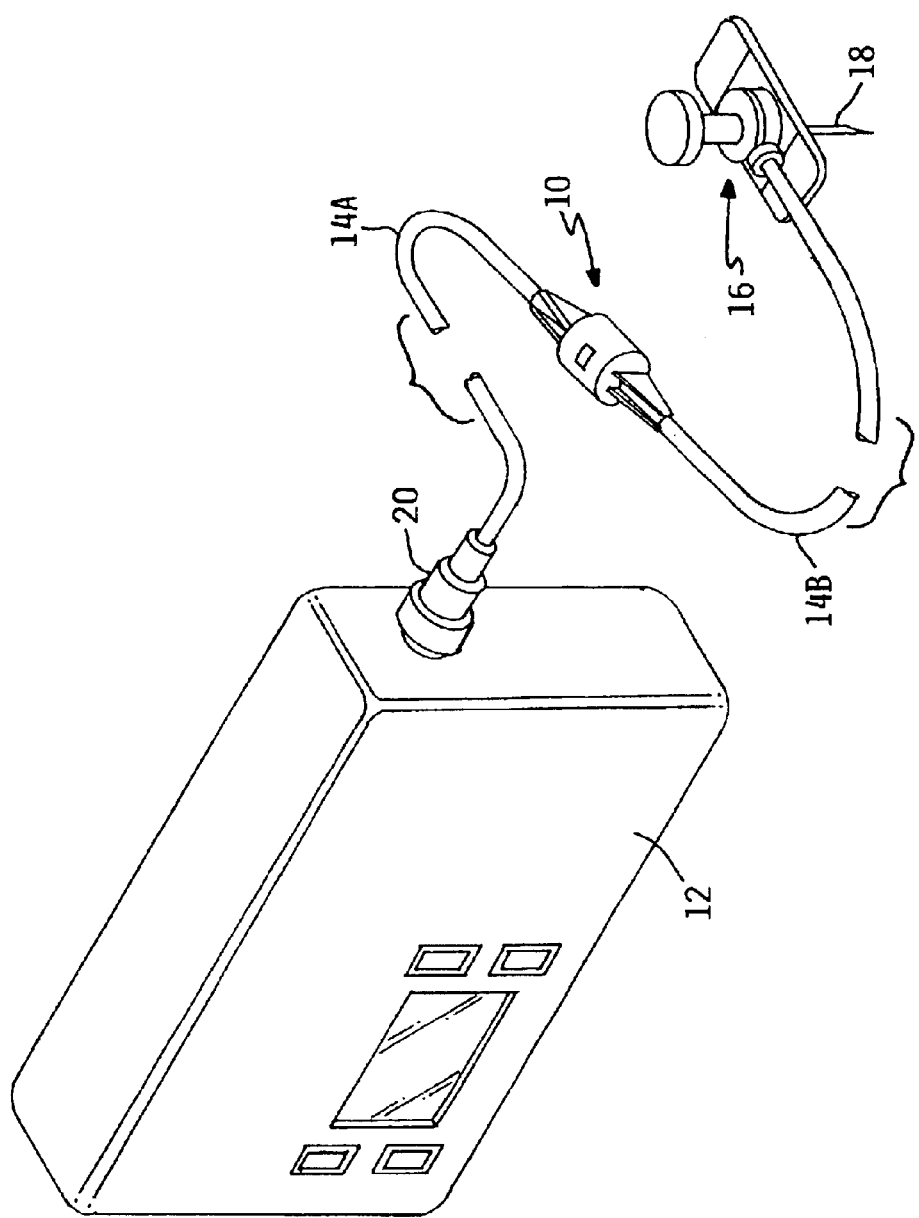
FIG. 1 is a prior art drawing, showing an infusion pump, an infusion set, and a tubing composite that comprises a quick-release coupling.

FIG. 1 illustrates a conventional medical infusion device 12. Such a medical infusion device typically comprises a computer (not shown) to control quantities and rates of infusion; buttons or other means for the patient to program or otherwise interact with the computer; room (not shown) for a reservoir (not shown) that contains the medication; a mechanical drive system (not shown), controlled by the computer, that pushes medication from the reservoir (not shown) through a a tubing composite comprising (in this particular exemplary drawing) a tubing 14A and a tubing 14B.

Figure 2A:
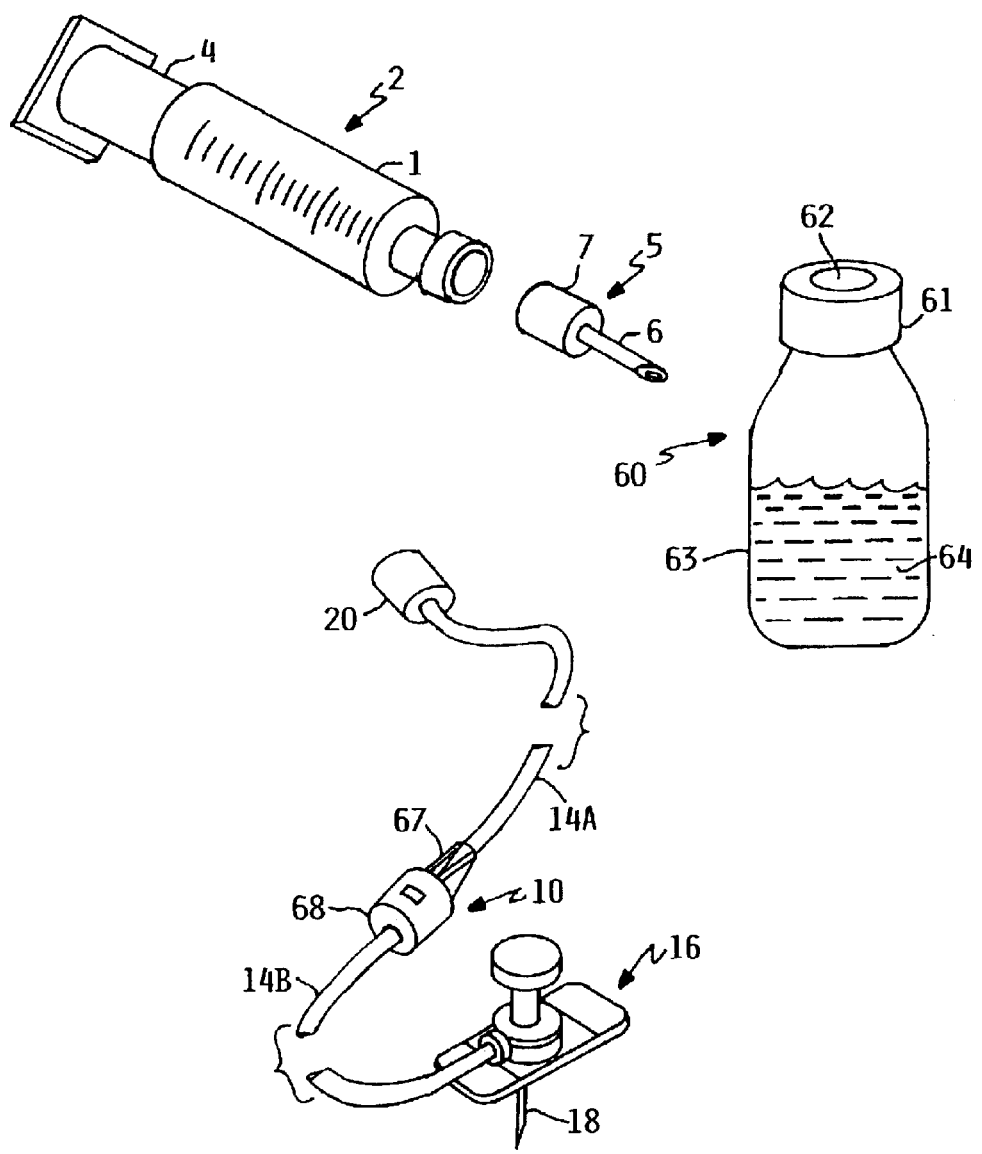
FIG. 2A is a prior art drawing, showing a reservoir, a reservoir syringe, a tubing, an infusion set, and a medication vial.

FIG. 2A shows the components that contain medication in a typical medication infusion system. The particular components are exemplary, and variations exist that perform like functions. The patient uses a medication vial 60 that contains medication 64. Medication vial 60 typically comprises a glass container 63 and a cap 61. Cap 61 further comprises a membrane 62 through which medication 64 will be drawn from medication vial 60. A reservoir 2 typically comprises a barrel 1 and a piston 4. A reservoir syringe 5 can be coupled to reservoir 2 using reservoir syringe coupling 7. Reservoir syringe 5 also comprises a needle 6. Tubing 14A can be coupled to reservoir 2 by coupling 20. Infusion set 16 is suitable for attachment to a patient using adhesive or other means. Infusion set 16 comprises cannula 18 that is inserted into the patient. Infusion set 16 further comprises infusion set tubing 14B. Infusion set tubing 14B has a first quick-release portion 68 that mates with a second quick-release portion 67 on a quick-release end of tubing 14A. The mated quick-release portions 67 and 68 are shown as quick-release coupling 10. In some embodiments, quick-release portion 68 is a part of infusion set 16, and infusion set tubing 14B is not used.

Figure 2B:
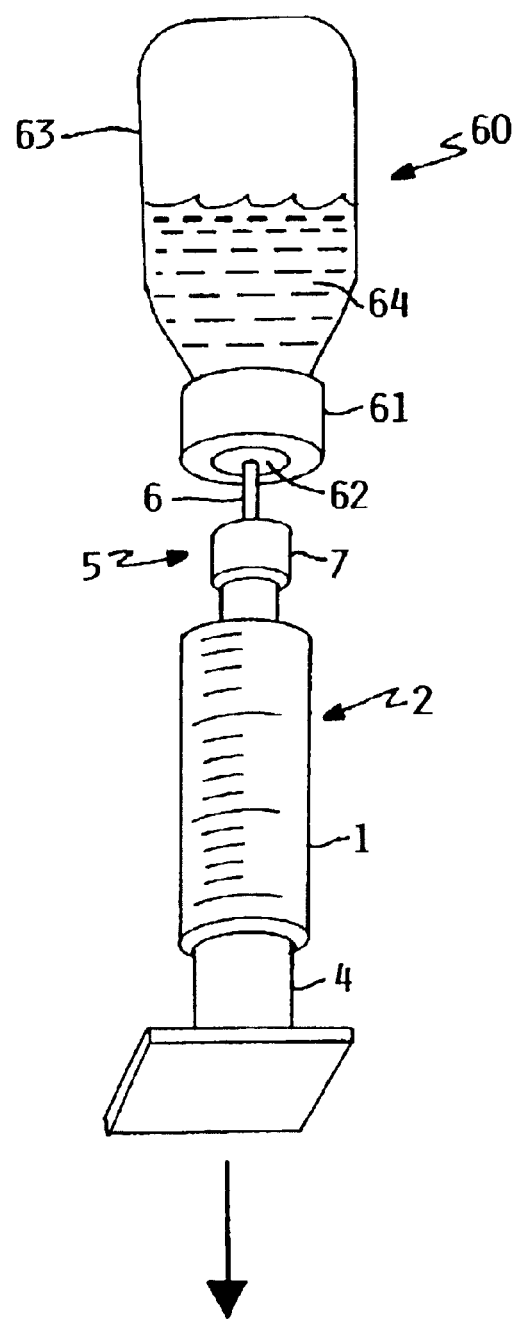
FIG. 2B is a prior art drawing showing medication being drawn from a medication vial into a reservoir through a syringe.

FIG. 2B shows how reservoir 2 is filled from medication vial 60. Reservoir syringe 5 is coupled to reservoir 2. Needle 6 is inserted through membrane 62, immersing the point of needle 6 in medication 64. Piston 4 is activated to draw medication through needle 6 into reservoir 2.

Figure 2C:
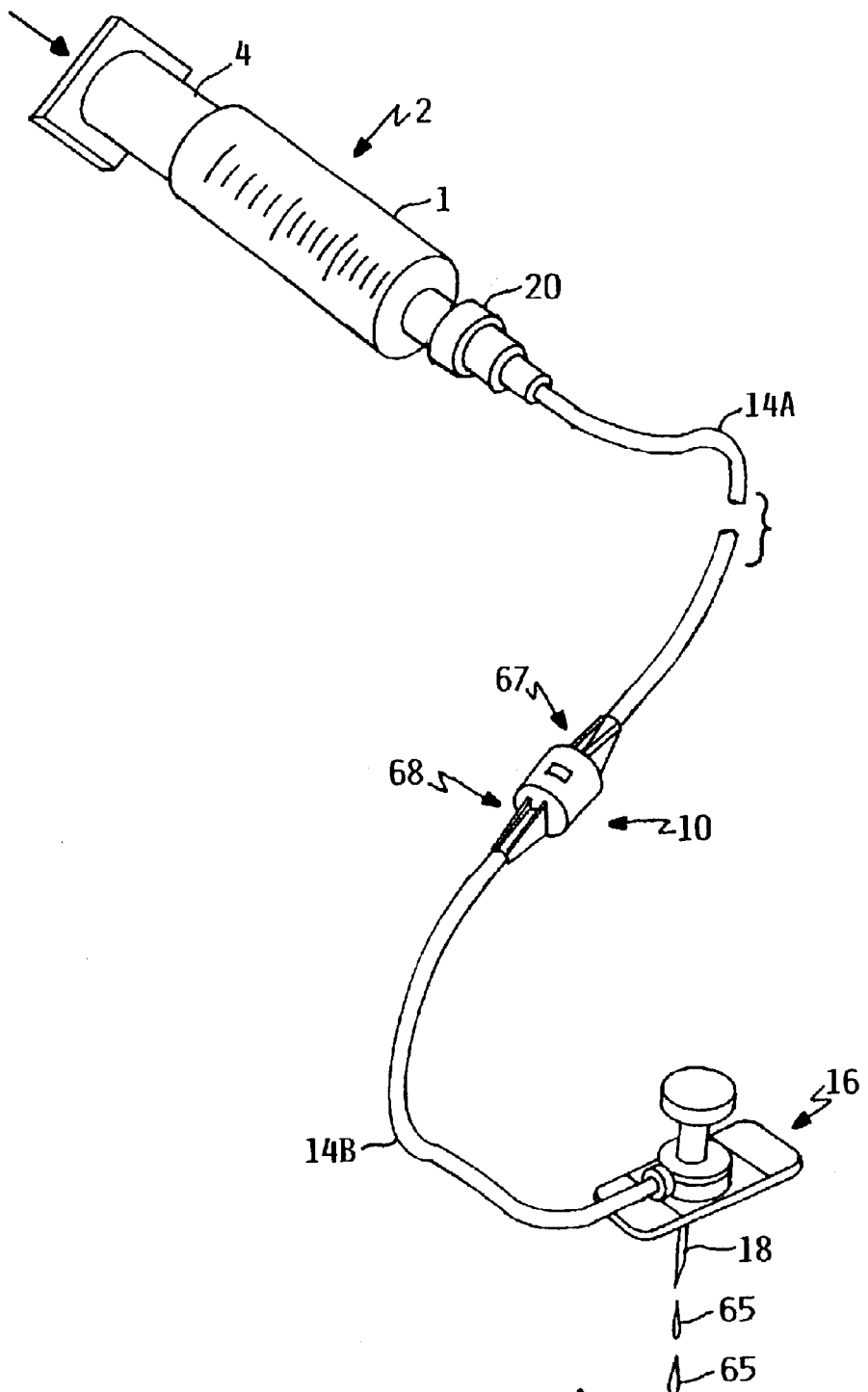
FIG. 2C is a prior art drawing showing a tubing composite and an infusion set being filled from a reservoir.

FIG. 2C shows how tubing 14A and infusion set tubing 14B are filled from reservoir 2 in a conventional method. Any combination of tubing coupled together through which medication flows from a reservoir to a patient is called a tubing composite. In the example above, the tubing composite comprises tubing 14A and infusion set tubing 14B.

Tubing 14A is coupled to reservoir 2 with coupling 20. Quick-release portions 67 and 68 are mated. Piston 4 is actuated, pushing medication from reservoir 2 into tubing 14A and infusion set tubing 14B. Appearance of medication drops 65 at the end of cannula occurs when tubing 14A and infusion set tubing 14B are full. Typically both tubing 14A and infusion set tubing 14B are transparent, allowing the patient to visually observe the progression of medication through tubing 14A and infusion set tubing 14B.

Figure 2D:
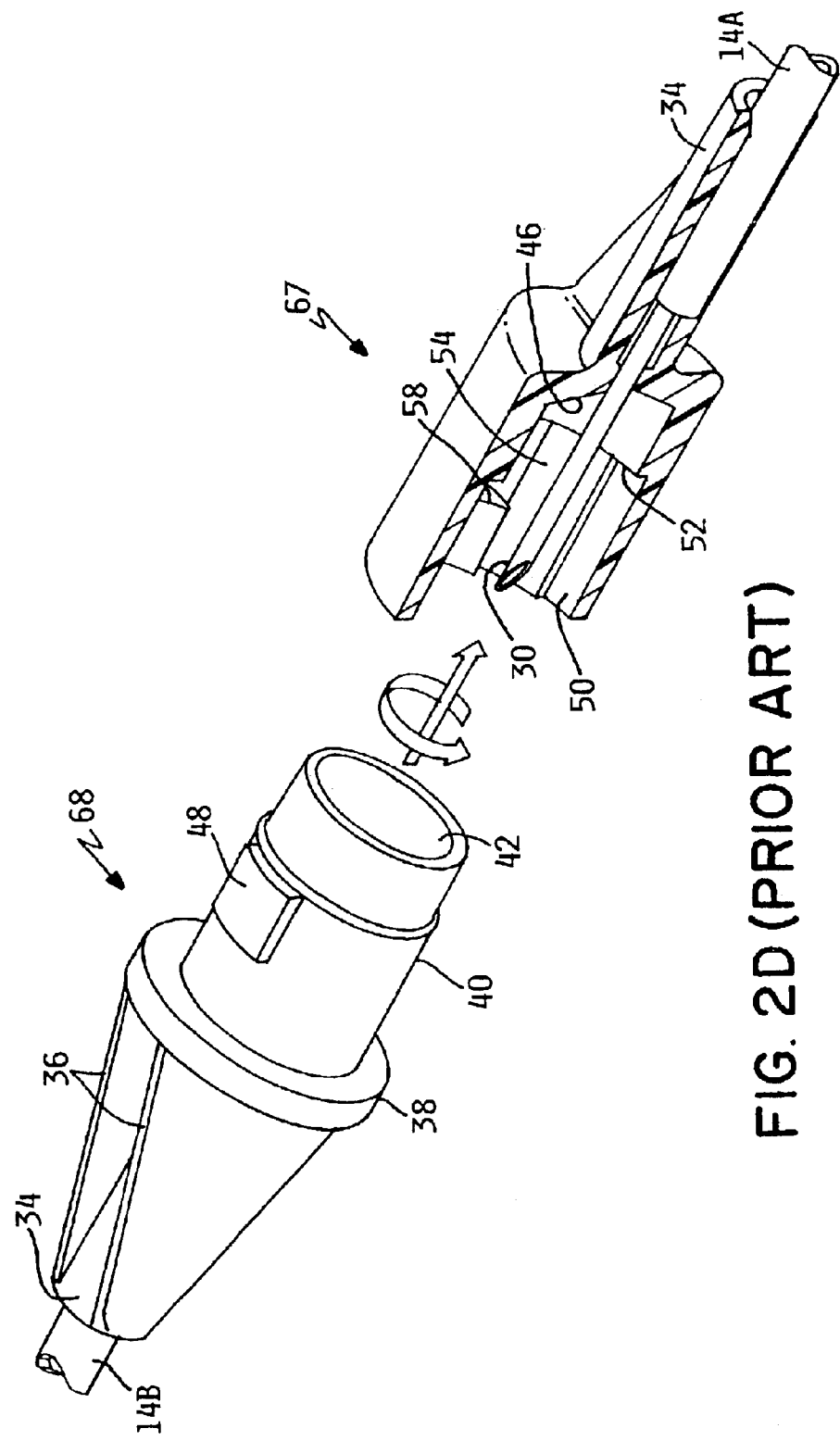
FIG. 2D is a prior art drawing showing insertion and activation of a quick-release coupling.

Note, in particular, that tubing 14A and infusion set tubing 14B are filled with medication from reservoir 2. After filling tubing 14A and infusion set tubing 14B, the original content of medication in reservoir 2 has been decreased by the quantity of medication required to fill tubing 14A and infusion set tubing 14B. The quantity of medication that can be infused into the patient is a quantity equal to the remaining quantity of medication in reservoir 2. For example, if the total volume of reservoir 2 is N cc (cubic centimeters), and the volume of the tubing composite is M cc, only a volume of (N–M) cc remains in reservoir 2 after filling the tubing composite with M cc. A full actuation of piston 4 can force no more than the remaining (N–M) cc from reservoir 2. Therefore, only a quantity of medication FIG. 2D shows a conventional quick-release coupling as described in Funderburk. First quick-release portion 68 mates into second quick-release portion 67 so that medication can flow from tubing 14A to infusion set tubing 14B. Remaining reference numbers in FIG. 2D refer to description in Funderburk.

Figure 3A:
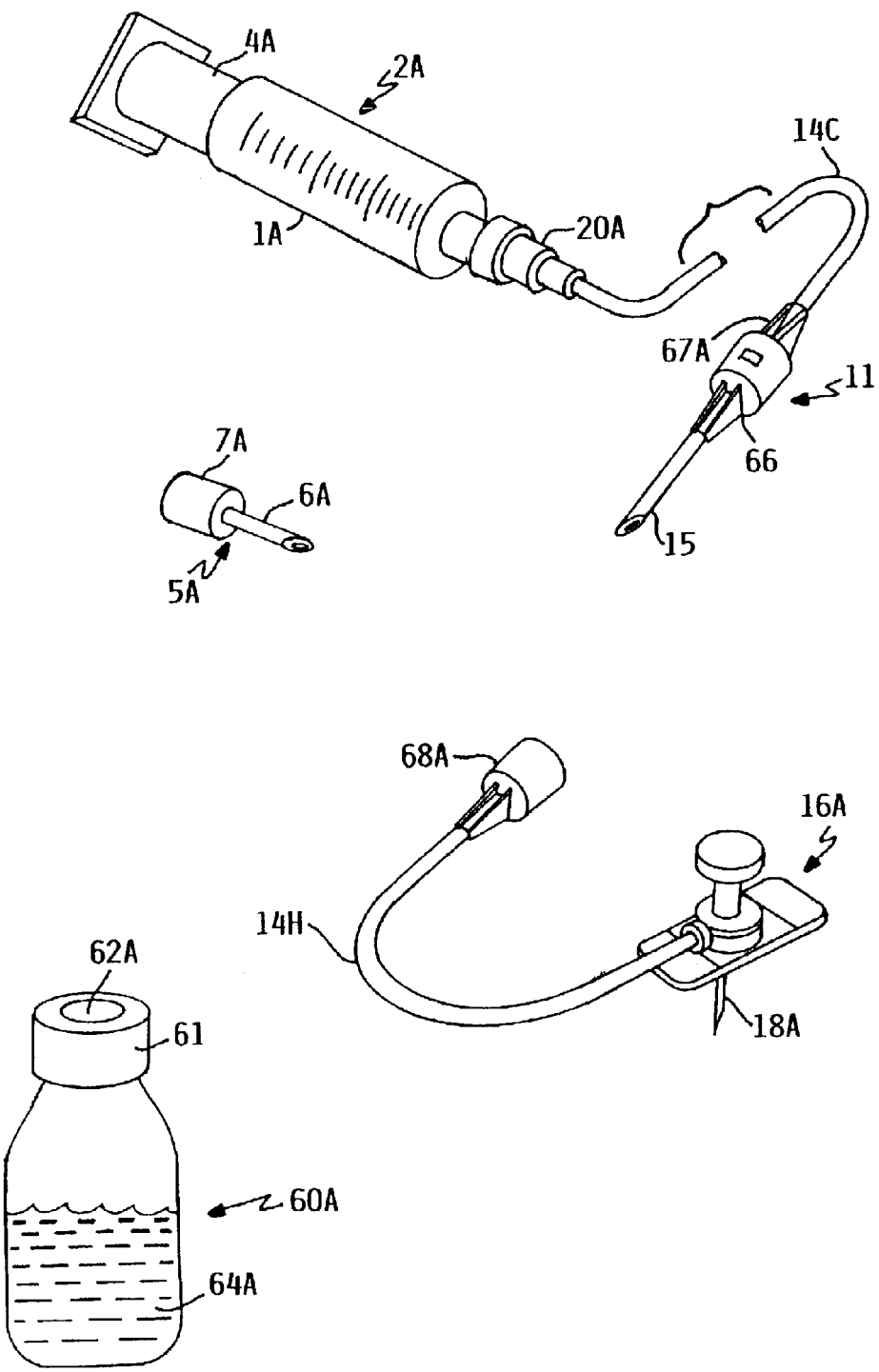
FIG. 3A is a drawing of a reservoir, a tubing, a quick-release syringe, a reservoir syringe, and an infusion set.

FIG. 3A illustrates a novel quick-release syringe 66. Quick-release syringe 66 is shown mated to a quick-release portion 67A, forming quick-release coupling 11. Quick-release syringe 66 is shown by itself and in more detail in FIG. 4A.

Quick-release portion 67A is advantageously the same as quick-release portion 67. Hereinafter, numeric references having alphabetic suffixes indicate items that are advantageously the same as the item referred to by the numeric reference.

Those skilled in the art will recognize that although quick-release coupling 11 shown is an example of a preferred quick-release coupling, any known or future means of quick-release coupling is within the spirit and scope of the present invention. Quick-release syringe 66 is shown coupled to a distal end of tubing 14C. Tubing 14C has coupling 20A at a proximal end, suitable for coupling with reservoir 2A. Reservoir 2A further comprises piston 4A and barrel 1A. FIG. 3A also shows reservoir syringe 5A. Reservoir syringe 5A comprises a reservoir coupling 7A and needle 6A. FIG. 3A also shows medication vial 60A, comprising cap 61A, membrane 62, and medication 64A.

Figure 3B:
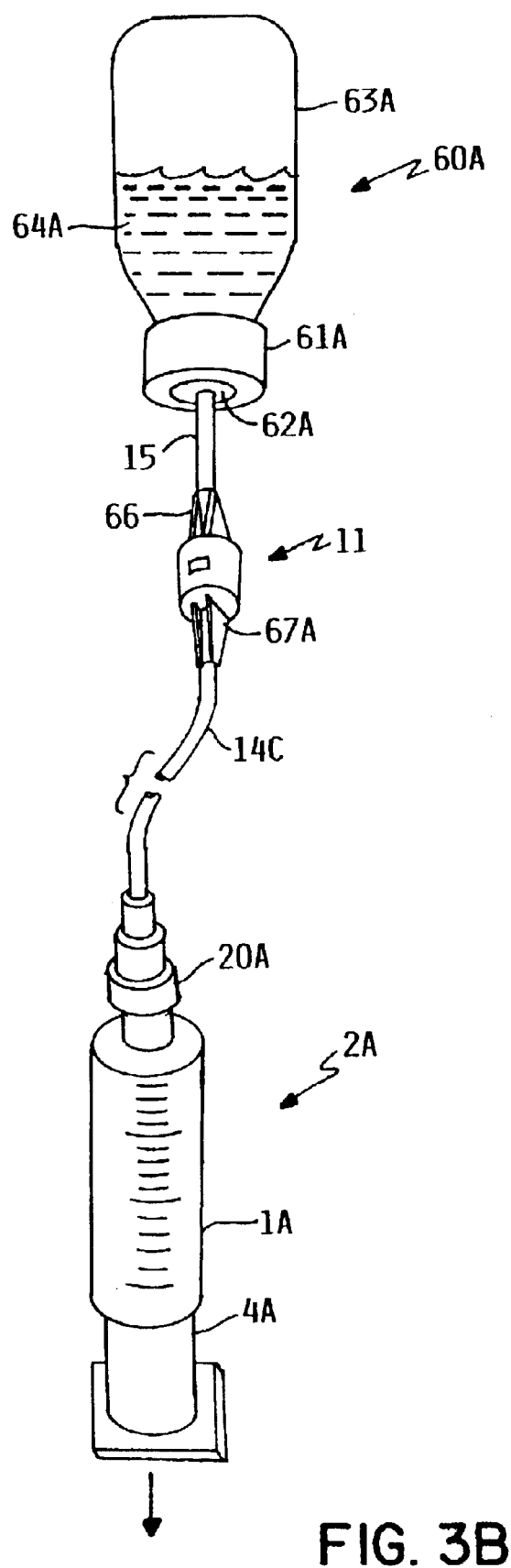
FIG. 3B is a drawing showing medication being drawn from the medication vial through a quick-release syringe into the tubing and the reservoir.

FIG. 3B shows how tubing 14C, and, optionally, a portion of reservoir 2A is filled using quick-release syringe 66. Quick-release syringe 66 is mated to quick-release portion 67A. Reservoir coupling 20A is coupled to reservoir 2A. Needle 15 of quick-release syringe 66 is inserted through membrane 62A such that the point of needle 15 is immersed in medication 64A in medicine vial 60A. Piston 4A is actuated, drawing medication through needle 15 into tubing 14C, filling tubing 14C, and, optionally, a portion of reservoir 2A.

Figure 4A:
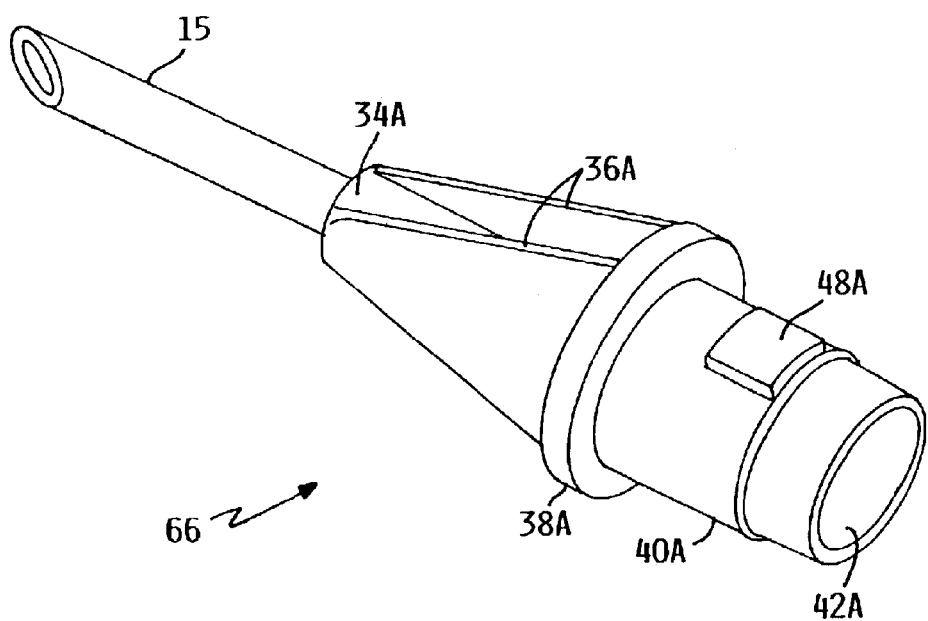
FIG. 4A shows a syringe quick-release male portion of a quick-release coupling.

FIG. 4A shows quick-release syringe 66 in an isometric view. Needle 15 protrudes from a distal end of quick-release syringe 66 so that it can be inserted into medicine vial 60A as described above. Other reference numbers 34A, 36A, 38A, 40A, 48A, and 42A perform as the corresponding reference number items 34, 36, 38, 40, 48, and 42 as described in Funderburk, which describes the mechanical elements that provide for mating with quick-release portion 67 or quick-release portion 67A.

Figure 4B:
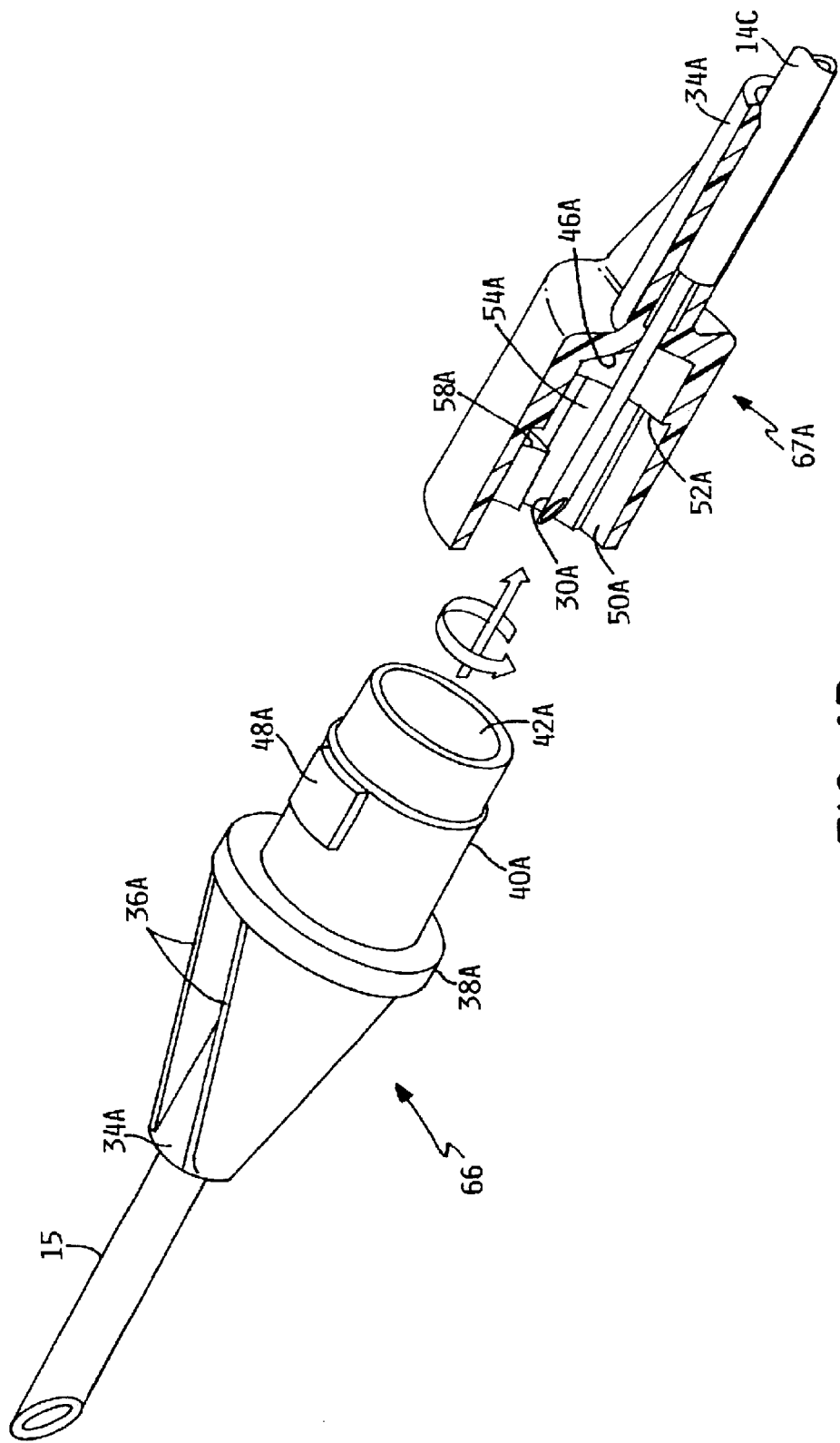
FIG. 4B shows insertion and activation of the male syringe quick-release portion into a female quick-release portion.

FIG. 4B shows the insertion/twisting mating action of quick-release syringe 66 with quick-release portion; 67A. Reference numbers 34A, 36A, 38A, 40A, 42A, 48A, 30A, 50A, 52A, 54A, 34A, 46A, and 58A are the same as elements as 34, 36, 38, 40, 42, 48, 30, 50, 52, 34, 46, and 58 described in U.S. Pat. No. 5,545,152.

While the above apparatus allows for filling a tubing, one must "top off" reservoir 2A with medication. "Topping off" simply means to fill to capacity. This method comprises decoupling tubing 14C from reservoir 2A and later recoupling tubing 14C to reservoir 2A after "topping off" reservoir 2A using reservoir syringe 5A. This method will be described in detail shortly. At this point, it is important to recognize that a small amount of air can be introduced into main tubing 14C and/or reservoir 2A during the process of decoupling and recoupling coupling 20A to reservoir 2A.

Figure 6:
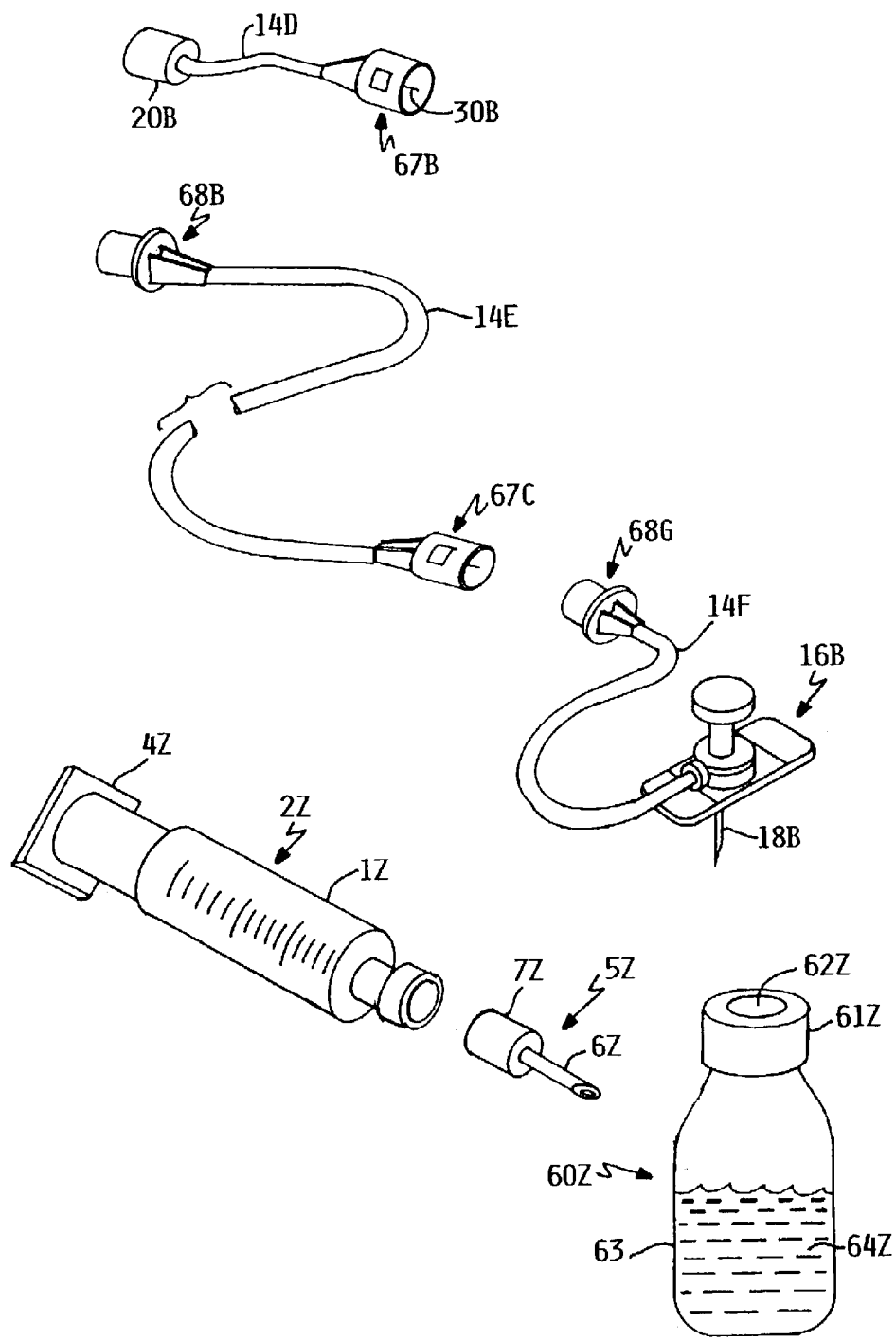
FIG. 6 shows an air elimination tubing, a tubing with a quick-release portion on each end, and an infusion set. A reservoir, a reservoir syringe, and a medication vial are also shown.

FIG. 6 shows an apparatus that can be used to eliminate such introduced air without substantially reducing the quantity of medication that can be infused into the patient.

FIG. 6 shows an air elimination tubing 14D that has reservoir coupling 20B on a proximal end and quick-release portion 67B at a distal end. Medication originally contained in air elimination tubing 14D will be partially or completely wasted; therefore, air elimination tubing 14D should be made short, with a volume preferably less than approximately 1% of the volume of reservoir 2Z. For example, the reservoir of the Paradigm® insulin infusion pump described earlier has a capacity of 1.76 cc, or 176 units of U-100 insulin. A suitable air eliminating tubing for use with the Paradigm® infusion pump would have a volume of approximately 0.02 cc (2 units), or less. Slightly longer air elimination tubings could be used, but would reduce the effectiveness of the invention. Continuing with the example of the Paradigm® infusion pump, if an air elimination tubing of 0.05 cc volume were used, the quantity of medication that can be infused would be reduced approximately 3%. Embodiments of even longer—and therefore larger volume—air elimination tubings are possible, and are within the spirit and scope of this invention, but further reduce the advantages of the present invention. Air elimination tubings having a volume of even 6% of the volume of a reservoir still allow a larger quantity of medicine to be infused into a patient than previous methods.

Tubing 14E has a quick-release portion 68B on a proximal end, and a second quick-release portion 67C on a distal end.

Note that the quick-release portion 67B has a connection needle 30B. This is advantageously the same connection needle 30 described in Funderburk, column 4, lines 55–65. As described, "A connector needle 30 has a proximal end seated within the infusion tubing segment, within the ferrule 26 of the female component 22." It is important that quick-release portion 67B have a connector needle 30 in order that air can be expelled from air elimination tubing 14D. For example, a quick-release portion 68B in the example, is advantageously the same as the male quick-release portion shown in FIG. 5 of Funderburk, which has self-sealing resilient septum 42 that is penetrated by connector needle 30 upon coupling. Air could not be driven from air elimination tubing 14D if such a male quick-release portion were to be used at the distal end of air elimination tubing 14D.

A tubing composite in the embodiment of FIG. 6 is formed by coupling tubing 14D, tubing 14E, and tubing 14F.

Reservoir 2Z, reservoir syringe 5Z, and medication vial 60Z are shown in FIG. 6, and will be further discussed shortly in discussion of a method embodiment.

Figure 7:
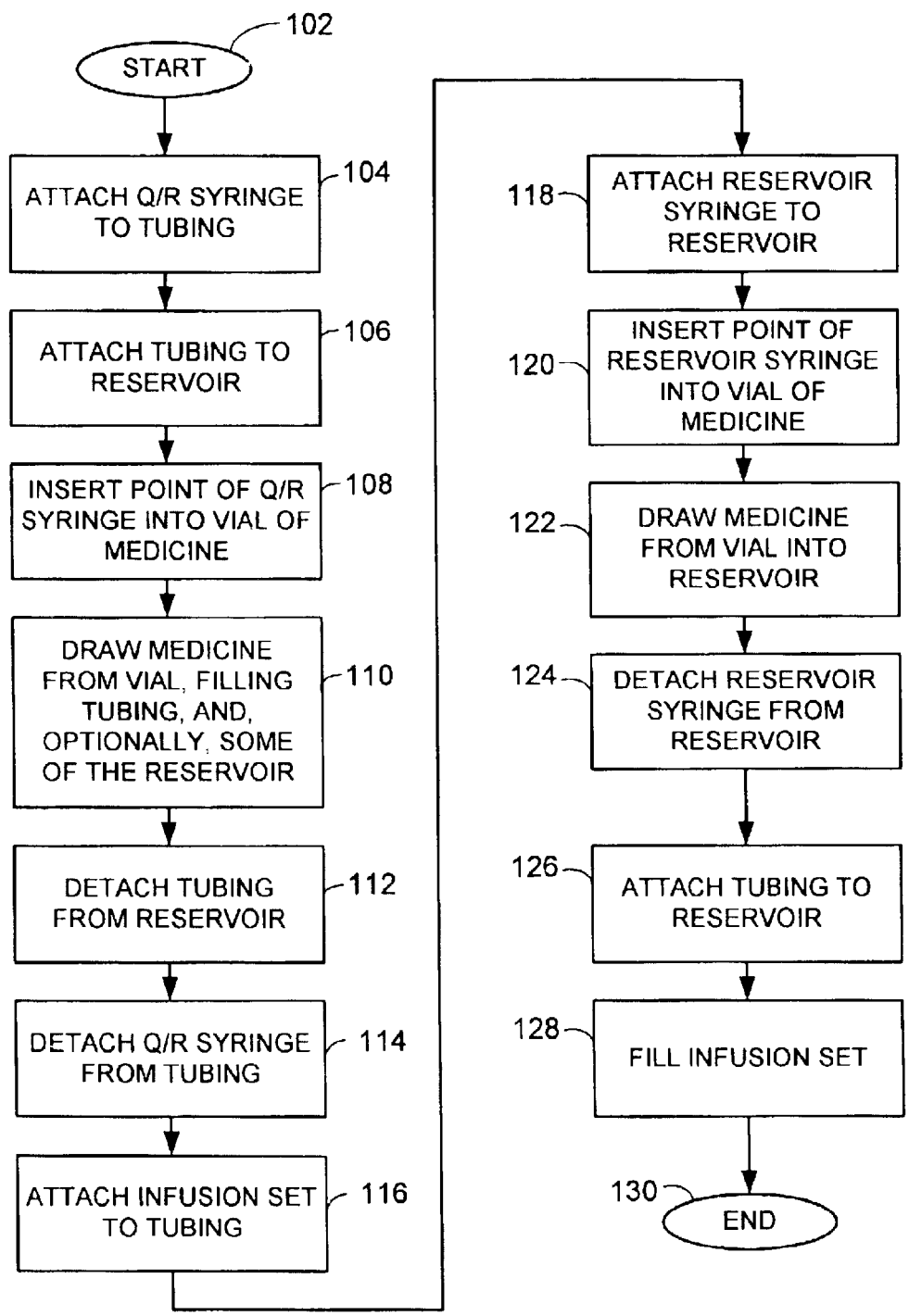
FIG. 7 is a flow chart showing an embodiment of a method of maximizing the use of the volume of a reservoir comprising steps taken to fill a tubing, and a portion of a reservoir from a vial of medication using a quick-release syringe at a distal end of the tubing.

FIG. 7 shows an embodiment of a method in which a reservoir and tubing are substantially completely filled, allowing a volume of medication substantially equal to the total volume of the reservoir to be infused into a patient.

Step 102 begins the method.

In step 104, quick-release syringe 66 (see FIG. 3A) is attached to a distal end of a tubing 14C. Any quick-release mechanism is intended to be within the spirit and scope of the invention. The tubing may be a single piece of tubing or may be a combination of several pieces of tubing coupled together, as discussed above. In general, one or more pieces of coupled tubings are referred to as a tubing composite. Tubing 14C is an exemplary tubing composite shown in FIG. 3A, comprising but a single section of tubing.

In step 106, a proximal end of the tubing composite is attached to reservoir 2A, making a coupling through which medicine can flow from reservoir 2A into the tubing composite.

In step 108, needle 15 of quick-release syringe 66 is inserted to medicine vial 60A such that the point of needle 15 is immersed in medication 64A in medicine vial 60A.

In step 110, piston 4A on reservoir 2A is actuated to draw medication from medication vial 60A, filling the tubing composite, and, optionally, some of the volume of reservoir 2A. Note that if piston 4A is fully actuated a quantity of air substantially equal to the volume of the tubing composite will have been drawn into reservoir 2A.

In step 112, the tubing composite is detached from reservoir 2A.

In step 114, quick-release syringe 66 is detached from the distal end of the tubing composite.

In step 116, infusion set 16A is coupled to the distal end of the tubing composite.

In step 118, reservoir syringe 5A is attached to reservoir 2A.

In step 120, needle 6A of reservoir syringe 5A is inserted into medicine vial 60A until the point of needle 6A is immersed in medication 64A.

In step 122, piston 4A is actuated, drawing medication from medicine vial 60A into reservoir 2A, filling it substantially to capacity.

In step 124, reservoir syringe 5A is detached from reservoir 2A.

In step 126, the tubing composite is again attached to reservoir 2A.

In step 128, infusion set 16A is filled with medication by actuating piston 4A. Volume of infusion set tubing 14F is typically less than 1% of the volume of reservoir 2A, and therefore does not require a significant quantity of medication to fill. Many infusion sets have their quick-release coupling physically part of the infusion set itself, rather than having an infusion set tubing 14F, so that the quantity of medication required to fill the infusion set is much less than 1% of the volume of reservoir 2A.

Step 130 completes the method. At this time infusion set 16A is applied to the patient, with cannula 18A inserted into the patient's body, and adhesive or tape (not shown) secures infusion set 16A to the patient's body. At step 130, both reservoir 2A and the tubing composite are substantially full, and therefore, a volume of medication substantially equal to the volume of medication in the reservoir can be infused into the patient.

Figure 5:
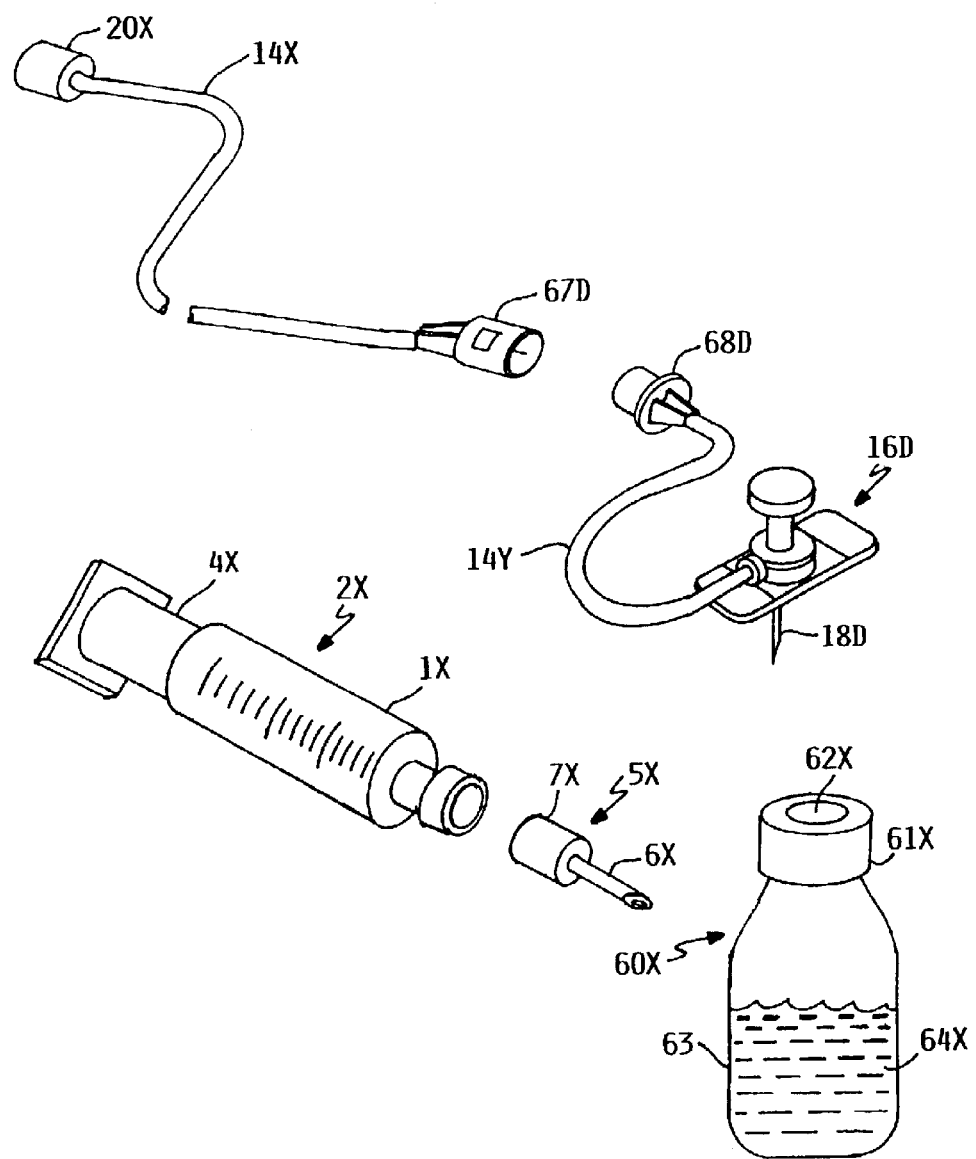
FIG. 5 shows a tubing, an infusion set, a reservoir, a reservoir syringe, and a medication vial.
Figure 8:
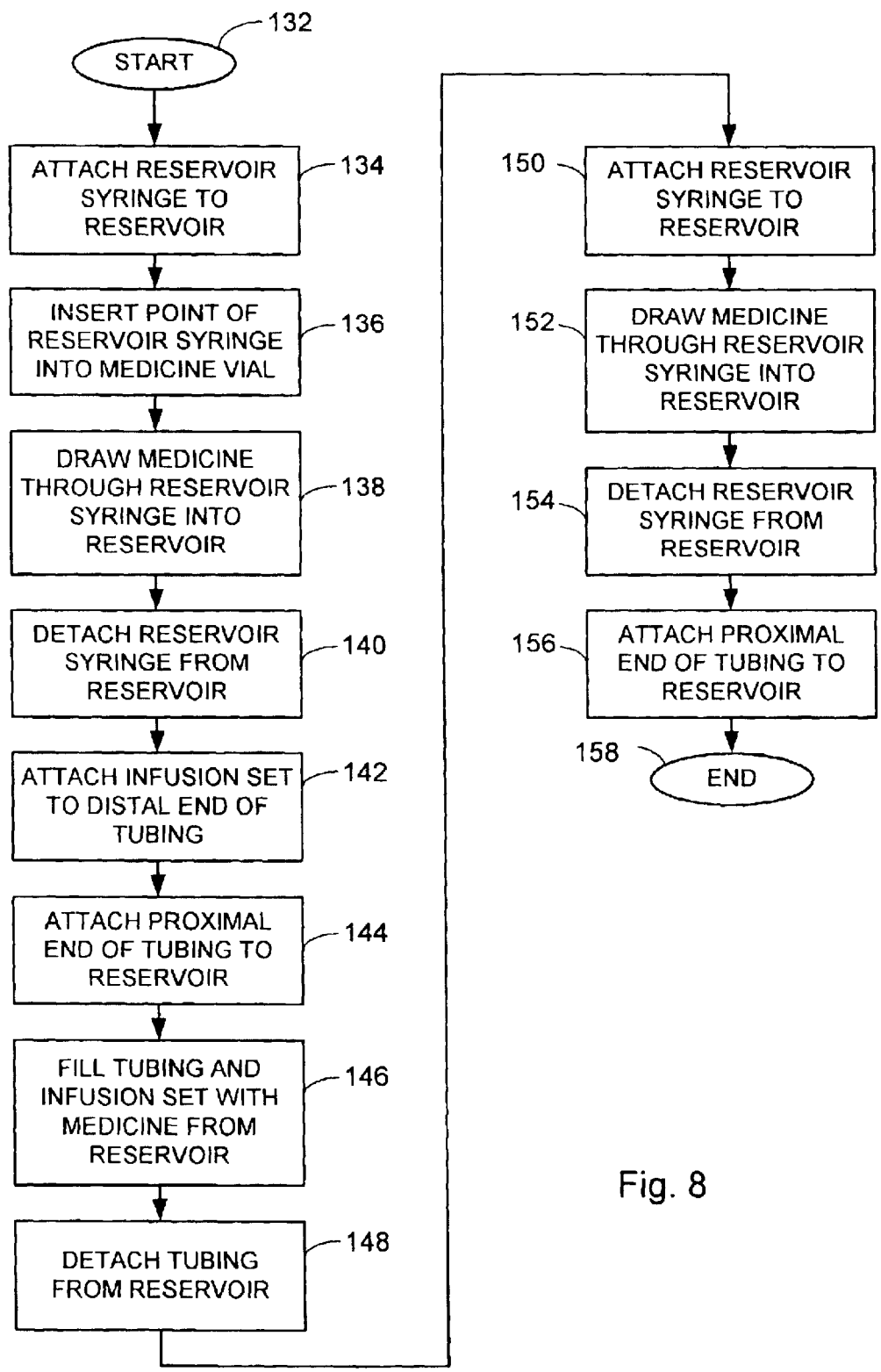
FIG. 8 is a flow chart showing an embodiment of a method of maximizing the use of the volume of a reservoir comprising steps taken to fill a tubing from the reservoir into a proximal end of the tubing.

FIG. 8 shows a second embodiment of the method, wherein a tubing composite is filled from a proximal end from the reservoir, in contrast to the previous embodiment wherein a tubing composite was filled from a distal end. FIG. 5 illustrates exemplary apparatus components used in this embodiment. Those skilled in the art will recognize that variations in the components can and do exist, and that there are many mechanisms that perform the functions of coupling a tubing to a reservoir, and many quick-release couplings that currently exist or which may be created in the future. The apparatus set shown is for exemplary purposes only, and is not to be construed as limiting.

Step 132 begins the second embodiment of the method.

In step 134, Reservoir syringe 5X is attached to reservoir 2X.

In step 136, needle 6X is inserted through membrane 62X into medicine vial 60X until the point of needle 6X is immersed in medication 64X.

In step 138, medication 64X is drawn through reservoir syringe 5X into reservoir 2X. Sufficient medication is drawn into reservoir 2X to substantially completely fill a tubing composite comprising tubing 14X, and, preferably infusion set tubing 14Y.

In step 140, reservoir syringe 5X is detached from reservoir 2X.

In step 142, infusion set 16D is coupled to a distal end of tubing 14X, using quick-release portions 67D and 68D. As noted before, many infusion sets have a quick-release portion as an integral part of the infusion set; others, as in FIG. 5, comprise an infusion set tubing 14Y between infusion set 16D and quick-release portion 68D. This invention is not limited to the exemplary apparatus of FIG. 5, but includes any infusion set and any quick-release coupling mechanism.

In step 144, a proximal end of tubing 14X is coupled to reservoir 2X.

In step 146, piston 4X is actuated, forcing medication from reservoir 2X into the tubing composite. The tubing composite at this step comprises tubing 14X and infusion set tubing 14Y. However, in another embodiment, infusion set 16D is coupled in a subsequent step, rather than prior step 142 above. Performing step 142 prior to step 146 is preferred, to avoid having to fill tubing 14Y from syringe 2X after it has been "topped off", which slightly reduces the quantity of medication that can be infused into the patient.

In step 148, the tubing composite is decoupled from reservoir 2X.

In step 150, reservoir syringe 5X is recoupled to reservoir 2X.

In step 152, medicine is drawn from medicine vial 64X into reservoir 2X, filling reservoir 2X substantially to capacity. That is, reservoir 2X is "topped off". Following this step, both the tubing composite and the reservoir are substantially both completely filled with medication.

In step 154, reservoir syringe 5X is detached from reservoir 2X.

In step 156, the proximal end of tubing 14X is recoupled to reservoir 2X.

Step 158 ends the method. After completing the steps in this method, both reservoir 2X and the tubing composite are full. The patient then inserts cannula 18D of infusion set 16D into his body and attaches infusion set to his body with tape or other adhesive in a conventional manner. A volume of medication substantially equal to the entirely filled volume of reservoir 2X can be infused into the patient.

While the embodiments above provide for the ability to infuse a volume of. medication into a patient that is substantially equal to the maximum volume of reservoir 2X, it is possible that a small amount of air is introduced into reservoir 2X and/or tubing 14X during the decoupling and recoupling steps. While small amounts of air are not harmful to the patient in medical infusion systems of this type, infusion of air instead of medication reduces the quantity of medication infused. For most patients, missing such a small amount of medication is not problematic; however, some patients are very sensitive to the medication and missing even a very small amount of medication can be significant to them.

Figure 9:
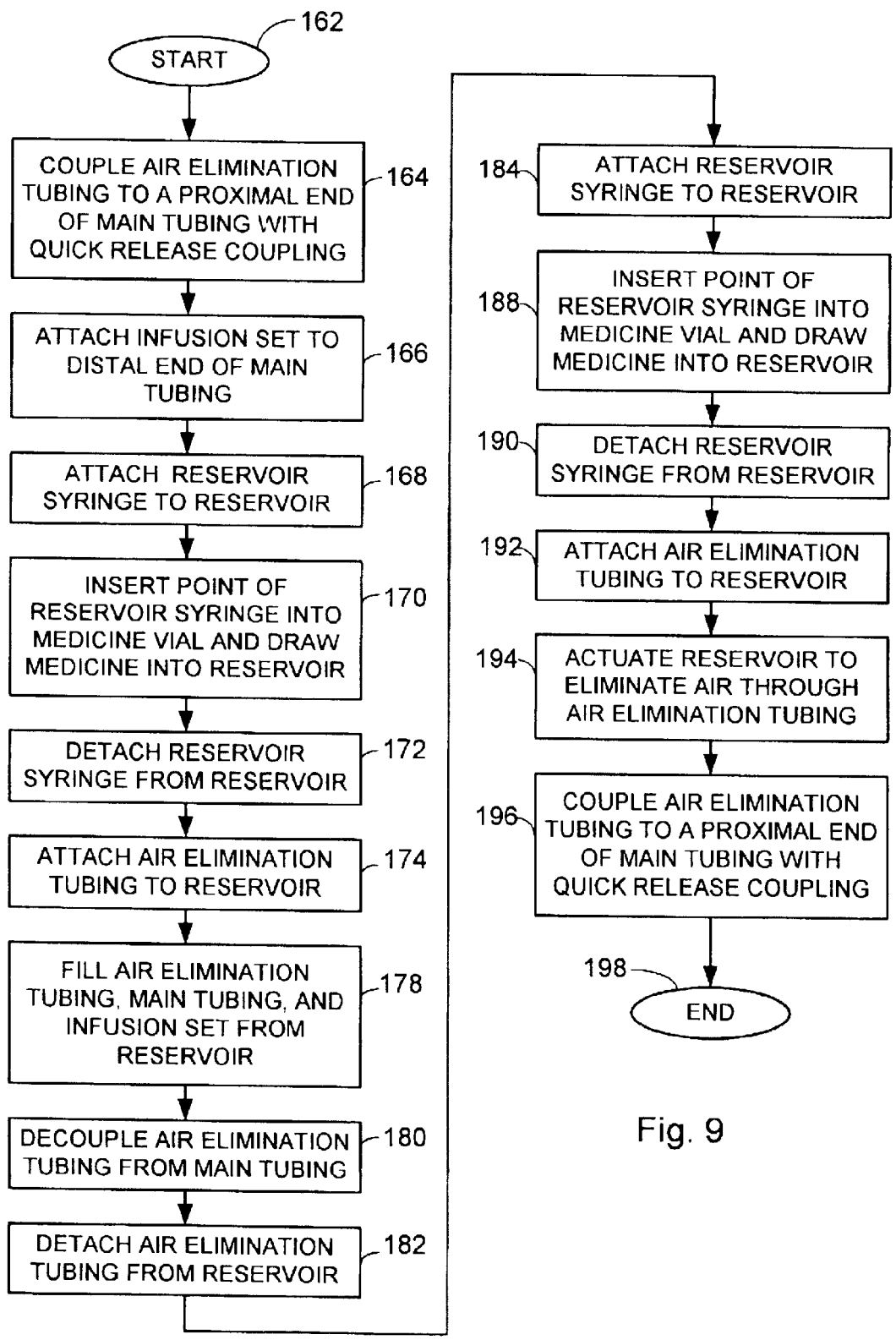
FIG. 9 is a flow chart showing an embodiment of a method used to maximize the use of the volume of a reservoir using an air elimination tubing.

FIG. 9 shows an exemplary set of steps to eliminate any air that be introduced during coupling of a tubing composite to the reservoir. The apparatus discussed in this method is illustrated in FIG. 6. Air eliminating tubing 14D is used in this method. This method is illustrated as an improvement over the embodiment illustrated in FIG. 8, but is just as applicable as an improvement over the embodiment illustrated in FIG. 7. In an embodiment, a tubing composite comprises air elimination tubing 14D and tubing 14E which has a quick-release portion on each end. As before, the tubing composite can further comprise infusion set tubing 14F associated with infusion set 16B. Coupling 20B is suitable for coupling to reservoir 2Z. Quick-release portion 67B mates with quick-release portion 68B. Quick-release portion 67C mates with quick-release portion 68G.

Step 162 starts the method.

In step 164, air elimination tubing 14D is coupled to tubing 14E by mating quick-release portions 67B and 68B.

In step 166, infusion set tubing 14F is added to the tubing composite comprising air elimination tubing 14D and tubing 14E by mating quick-release portions 67C and 68G.

In step 168, reservoir syringe 5Z is coupled to reservoir 2Z.

In step 170, needle 6Z is inserted through membrane 62Z and the point of needle 5Z is immersed in medication 64Z in medication vial 60Z. Medication is drawn into reservoir 2Z by actuating piston 4Z. Sufficient medication must be drawn into reservoir 2Z to completely fill the tubing composite.

In step 172, reservoir syringe 5Z is decoupled from reservoir 2Z.

In step 174, the tubing composite is coupled to reservoir 2Z by coupling 20B.

In step 178, piston 4Z is actuated, forcing medication into the tubing composite, substantially filling the tubing composite with medication from reservoir 2Z.

In step 180, air elimination tubing 14D is decoupled from the remainder of the tubing composite by decoupling quick-release portions 67B and 68B.

In step 182, air eliminating tubing 14D is decoupled from reservoir 2Z by 25 disconnecting coupling 20B from reservoir 2Z.

In step 184, reservoir syringe 5Z is reattached to reservoir 2Z.

In step 188, needle 6Z is inserted again through membrane 62Z and the tip of needle 6Z is immersed in medication 64Z in medication vial 60Z. Piston 4Z is actuated to substantially completely fill reservoir 2Z.

In step 190, reservoir syringe 5Z is again detached from reservoir 2Z.

In step 192, air elimination tubing 14D is reattached to reservoir 2Z by coupling 20B.

In step 194, reservoir 2Z is held substantially vertically with piston 4Z at the bottom in order that any air floats and gathers near coupling 20B. Piston 4Z is actuated, forcing the air bubble through air elimination tubing and out of quick-release portion 67B, which is not coupled to tubing 14E during this step.

In step 196, air elimination tubing 14D is again coupled to the remainder of the tubing composite. At this point, the tubing composite is filled with medication. Reservoir 2Z is also filled to capacity with medication, except for a small amount of medication lost during step 194 in eliminating the air bubble. Air elimination tubing 14D is relatively short in comparison to the remainder of the tubing composite, and preferably contains less than 1% of the capacity of the reservoir.

While the present invention has been described with reference to the details of the embodiments of the invention shown in the drawings, these details are not intended to limit the scope of the invention as claimed in the appended claims.

What is claimed is:

1. A method of making a quantity of medication, substantially equal to the total volume of a reservoir in a medical infusion device, available for infusion into a patient, comprising the steps of:

filling substantially all of the volume of said reservoir with a first quantity of medication;

filling substantially all of the volume of a tubing composite with a second quantity of medication; and coupling the tubing composite to the reservoir wherein the step of filling substantially all of the volume of said tubing composite with said second quantity of medication further comprises the steps of:

drawing medication into the tubing composite from a distal end of the tubing composite;

attaching a quick-release syringe to the distal end of the tubing composite;

coupling a proximal end of the tubing composite to the reservoir;

inserting a needle portion of the quick-release syringe into a vial of medication; and actuating a piston portion of the reservoir to draw medication from the vial of medication, through the quick-release syringe, and fill substantially all of the tubing composite.

2. The method of claim 1, wherein the step of filling substantially all of the volume of the reservoir with the first quantity of medication comprises the steps of:

attaching a reservoir syringe to the reservoir;

inserting a needle portion of the reservoir syringe into the vial of medication; and actuating before piston portion of the reservoir to draw medication from the vial or medication through the reservoir syringe, and fill substantially all of the capacity of the reservoir.

3. The method of claim 1, wherein the step of filling substantially all of the volume of the tubing composite with said second quantity of medication further comprises the step of forcing medication into said proximal end of the tubing composite.

4. The method of claim 3, wherein the step of forcing medication into said proximal end of the tubing composite further comprises the steps of:

attaching a reservoir syringe to the reservoir;

inserting a needle portion of the reservoir syringe into the vial of medication;

actuating said piston portion of the reservoir and drawing sufficient medication from the vial of medication into the reservoir to fill the tubing composite;

detaching the reservoir syringe from the reservoir;

coupling the proximal end of the tubing composite to the reservoir; and actuating the piston portion of the reservoir to force medication into the proximal end of the tubing composite.

5. The method of claim 4, further comprising the step of including an infusion set portion of the tubing composite.

6. The method of claim 3, wherein the step of filling substantially all of the volume of the reservoir further comprises the steps of:

attaching a reservoir syringe to the reservoir;

inserting a needle portion of the reservoir syringe into the vial of medication; and actuating said piston portion of the reservoir to draw medication from the vial of medication, filling substantially all of the volume of the reservoir.

7. The method of claim 1, further comprising the steps of:

coupling an air elimination tubing as a portion of the tubing composite, a proximal end of the air elimination hose suitable for coupling with the reservoir;

after filling substantially all of the volume of the reservoir with the first quantity of nedication, and filling substantially all of the volume of said tubing composite with a said second quantity of medication, decoupling the air elimination hose portion of the tubing composite from a remaining portion of the tubing composite;

actuating said piston portion of the reservoir to force air in the reservoir or in the air elimination tubing from a distal end of the air elimination hose; and recoupling the air elimination tubing to the remaining portion of the tubing composite.

* * * * *

UNITED STATES PATENT AND TRADEMARK OFFICE
CERTIFICATE OF CORRECTION

PATENT NO. : 6,786,244 B1
DATED : September 7, 2004
INVENTOR(S) : Steven Paul Jones It is certified that error appears in the above-identified patent and that said Letters Patent is hereby corrected as shown below:

Column 13,
Line 32, "before" should be -- a --.
Line 33, "or" should be -- of --.

Column 14,
Line 28, "nedication" should be -- medication --.
Line 30, delete "a".

Signed and Sealed this

Seventh Day of December, 2004

JON W. DUDAS
*Director of the United States Patent and Trademark Office*